(12) United States Patent
Neubauer et al.

(10) Patent No.: US 8,211,094 B2
(45) Date of Patent: Jul. 3, 2012

(54) PRE-CALIBRATED REUSABLE INSTRUMENT

(75) Inventors: Timo Neubauer, Feldkirchen (DE); Norman Plassky, Erfurt (DE)

(73) Assignee: Brainlab AG, Feldkirchen (DE)

( * ) Notice: Subject to any disclaimer, the term of this patent is extended or adjusted under 35 U.S.C. 154(b) by 2016 days.

(21) Appl. No.: 11/259,636

(22) Filed: Oct. 26, 2005

(65) Prior Publication Data

US 2006/0104707 A1    May 18, 2006

Related U.S. Application Data

(60) Provisional application No. 60/645,401, filed on Jan. 19, 2005.

(30) Foreign Application Priority Data

Oct. 26, 2004   (EP) ..................................... 04025401

(51) Int. Cl.
*A61B 19/00* (2006.01)
(52) U.S. Cl. ............................................ 606/1
(58) Field of Classification Search .............. 606/10–12, 606/1; 600/420–426
See application file for complete search history.

(56) References Cited

U.S. PATENT DOCUMENTS

| 5,267,993 | A  | * | 12/1993 | Grace et al. ...................... 606/11 |
| 6,190,395 | B1 | * | 2/2001  | Williams ........................ 606/130 |
| 2003/0208122 | A1 | * | 11/2003 | Melkent et al. ............... 600/426 |
| 2004/0068179 | A1 |   | 4/2004  | Jutras et al. |
| 2004/0158260 | A1 |   | 8/2004  | Blau et al. |
| 2006/0030771 | A1 | * | 2/2006  | Levine et al. ................. 600/424 |

FOREIGN PATENT DOCUMENTS

| FR | 2 830 743 | 4/2003 |
| WO | 01/67979 | 9/2001 |
| WO | 03/061501 | 7/2003 |
| WO | 2004/016178 | 2/2004 |

* cited by examiner

*Primary Examiner* — David Shay
(74) *Attorney, Agent, or Firm* — Renner, Otto, Boisselle & Sklar, LLP

(57) ABSTRACT

A pre-calibrated reusable instrument includes an instrument holder and an instrument held by and movable with respect to the instrument holder. The instrument includes at least two functional elements and at least three markers, wherein at least one of the markers is movable with the instrument relative to the instrument holder such that a movement of the instrument produces a corresponding movement of the at least one marker.

16 Claims, 2 Drawing Sheets

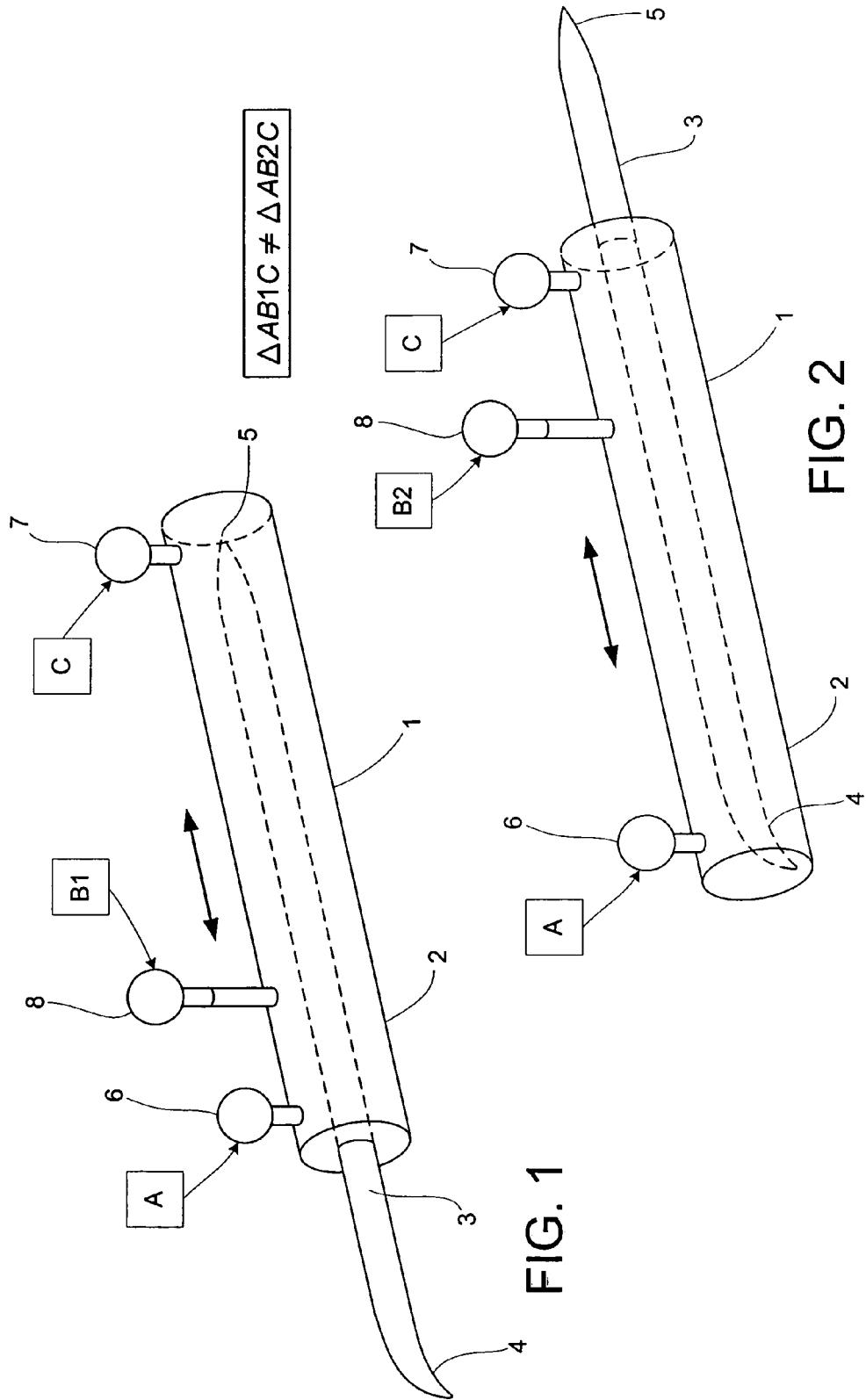

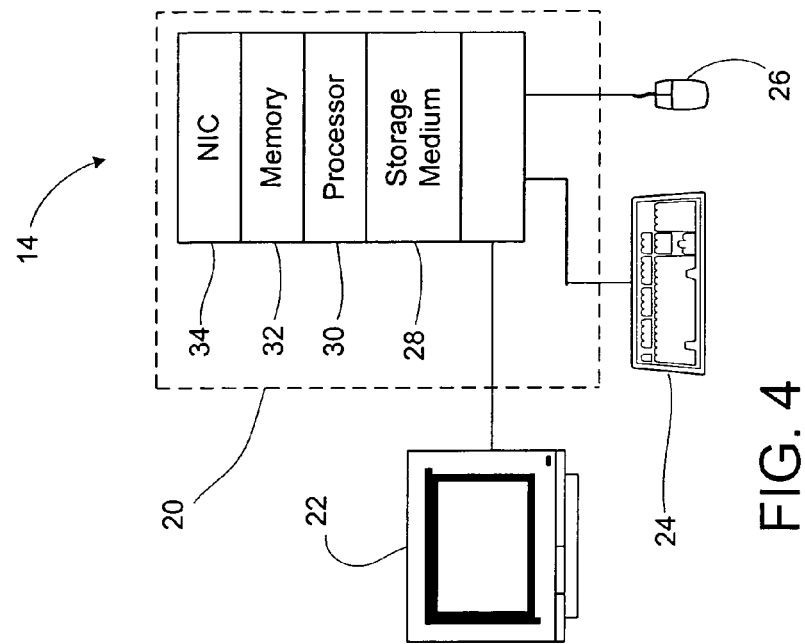
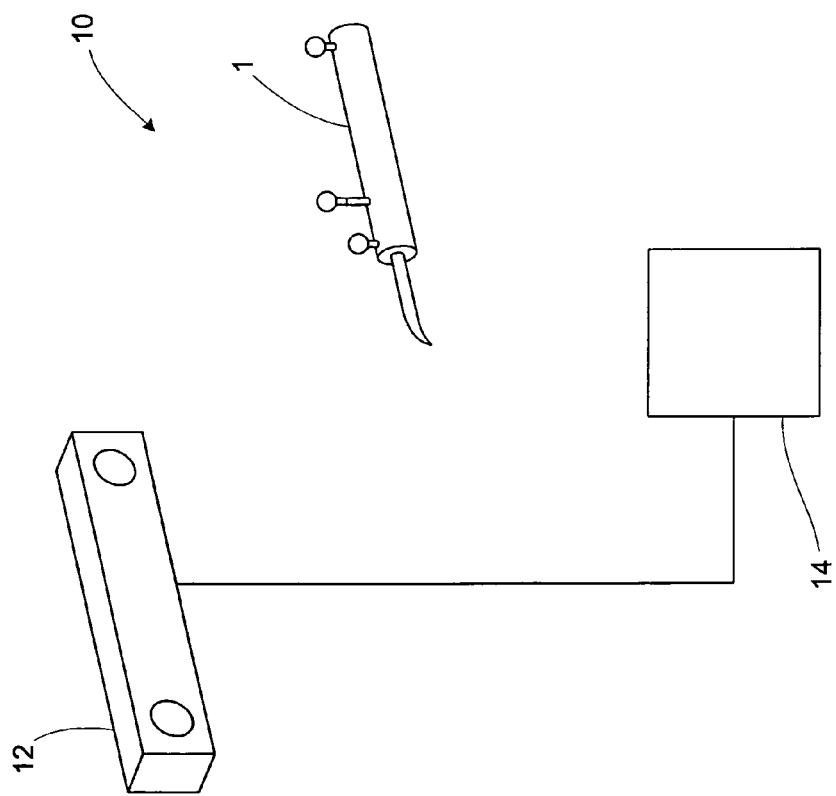
FIG. 4
FIG. 3

PRE-CALIBRATED REUSABLE INSTRUMENT

RELATED APPLICATION DATA

This application claims priority of U.S. Provisional Application No. 60/645,401 filed on Jan. 19, 2005, which is incorporated herein by reference in its entirety.

FIELD OF THE INVENTION

The present invention relates to medical instruments and, more particularly, to an apparatus and method for identifying pre-calibrated reusable instruments.

BACKGROUND OF THE INVENTION

Instruments that can perform a registering procedure generally include a fixed marker arrangement with passive or active markers, wherein the geometry of the marker arrangement can be identified by a navigation system. Using the geometry of the marker arrangement, it is possible to deduce the type or nature of the instrument. Various registering instruments exist for various applications, wherein each instrument is individually calibrated and must be registered or identified by the navigation system.

SUMMARY OF THE INVENTION

A pre-calibrated reusable instrument is provided that can include a plurality of instruments, wherein the plurality of instruments can be used, for example, to register bones or the like during medical procedures, such as a surgical procedure. Markers can be arranged on the pre-calibrated instrument, and their relative position with respect to each other can be identified by a navigation system. Once identified, the navigation system can deduce a location of a tip or pre-calibrated end of the instrument and/or of the plurality of instruments.

Further, there is provided a method for identifying the state of a pre-calibrated reusable instrument, wherein a relative position of markers with respect to each other is identified. By comparing the identified marker geometry with previously stored marker geometries, it is possible to deduce which instrument of the pre-calibrated reusable instrument can or is being used and/or is protruding from a casing, for example.

As used herein, pre-calibrating is understood to mean that the geometry of the reusable instrument is known or that data describing the geometry of the reusable instrument is known, wherein the known geometry and/or data are provided to or ascertained by a navigation system (or software of the navigation system) and can be stored in memory (e.g., a memory buffer). The data can include: positional and/or length details that, for example, identify the tips, ends or functional elements of the reusable instrument; the length of the reusable instrument; the position of the tips, ends or functional elements of the reusable instrument; and/or a shape of the tips, ends or functional elements of the reusable instrument.

The data describing the geometry of the pre-calibrated reusable instrument also can include information on the position of the markers on the pre-calibrated reusable instrument, and which marker arrangement or marker geometry corresponds to which functional element. The data can further include a possible use of a functional element. Accordingly, a navigation system, for example, can detect a marker geometry, from which it is possible to directly deduce which of the functional elements can, are, or should be used, or the shape of the usable functional element.

The pre-calibrated reusable instrument includes an instrument holder on or in which an instrument can be arranged, wherein the instrument can be moved relative to the instrument holder. The pre-calibrated instrument can further include at least three markers (e.g., active and/or passive markers), wherein at least one of the markers can be moved together with the instrument relative to the instrument holder. Thus, at least one of the markers can be connected to the instrument or arranged directly on the instrument, for example, such that the marker can be moved by a vector of the same direction and magnitude as the instrument, or such that the distances by which the marker and the instrument are shifted correspond in terms of direction and length. At least two of the markers can be connected to the instrument holder or can be fixedly or immovably arranged directly on the instrument holder, such that when the instrument is shifted relative to the instrument holder, the instrument and the marker connected to the instrument can perform a movement relative to the instrument holder and the at least two markers connected to the instrument holder.

The instrument can include at least two functional elements, such that the instrument exhibits the same functionality as at least two instruments each having one functional element or unit, wherein the functional elements of the instrument are preferably configured differently. The instrument can be held by the instrument holder and can be moved relative to the instrument holder and/or relative to the at least two markers connected to the instrument holder. The instrument holder can be configured as a hollow cylinder, wherein the instrument can be in the hollow or interior portion of the cylinder. Preferably, the instrument is mounted within the instrument holder such that it can be shifted with respect to the instrument holder. Further, the instrument also can be shifted along a longitudinal axis of the pre-calibrated reusable instrument or the instrument holder (e.g., along the longitudinal axis of the hollow cylindrical instrument holder). The instrument holder also can serve as a grip for the pre-calibrated reusable instrument.

The instrument, for example, together with the at least one marker connected to the instrument, can be moved or shifted relative to the instrument holder and/or relative to the markers connected to the instrument holder, wherein the instrument can be mounted non-rotatably in the instrument holder. This can ensure that movement of the instrument relative to the instrument holder is substantially constant and, in particular, that a translational movement is substantially constant and repeatable (e.g., moving or shifting is accomplished with tight positional tolerances).

The instrument, which preferably lies in the instrument holder, can be moved relative to the instrument holder into two fixed end states wherein, for example, the instrument locks in the end states and cannot be further moved or shifted until the end state is released (e.g., releasing a latch), at which point the instrument can be moved again. In particular, the end states of the instrument can be safety-locked, such that the instrument cannot be moved as long as the safety lock is activated or set, and can only be shifted relative to the instrument holder once the safety lock has been deactivated or released. The at least two functional elements of the instrument can be identical, similar or different, can have the same, similar or different functionality, and can be pre-calibrated. It can be known that the functional elements perform a particular function, can be situated on the instrument, or which functional element can, is or should be used with a particular marker arrangement or geometry. Thus, for example, a navigation system can detect or identify the respective marker geometry and can deduce from the marker geometry (wherein at least two markers can be connected to the instrument holder and at least one marker can be connected to the instrument) which functional element should be used or which functional element can be used or is available for use.

If, for example, two markers (e.g., active and/or passive markers) are connected to the instrument holder, and if one marker is connected to the instrument and the instrument includes two functional elements, then in one state of the pre-calibrated reusable instrument (e.g., in one fixed end state) the markers can form a particular marker geometry that indicates which of the two functional elements should be used or is ready to be used, for example. In a second state of the pre-calibrated reusable instrument, the markers can form another particular geometry, from which it can be deduced that the second functional element can be used or is ready to be used.

A registering procedure using the pre-calibrated reusable instrument can be performed wherein the reusable instrument is detected by a camera, such as an infrared camera, for example. The spatial position of the pre-calibrated reusable instrument can be ascertained, thereby enabling use of the at least two functional elements (which can have different shapes and can be used for registering different parts of the body, such as different bones or bone shapes) as registering instruments. A registering apparatus such as the pre-calibrated reusable instrument can be sufficient for performing various or multiple tasks. In contrast, conventional methods require the use of a number of instruments, such as registering apparatus or pointers, each of which have to be individually registered prior to use for registering bones or bone contours. The pre-calibrated reusable instrument, for example, is registered once. Thereafter, the pre-calibrated reusable instrument can be navigated by a navigation system, wherein due to the marker geometry, the navigation system and/or a computational unit can identify which functional element of the pre-calibrated reusable instrument is or should be used. Since all the functional elements are pre-calibrated, the functional element provided for use can be used for registering bones or bone contours. A calibrating procedure also can be sufficient to calibrate the reusable instrument together with the at least two functional elements, whereas when using a number of instruments each having one functional element, each instrument has to be individually calibrated.

The at least two functional elements of the instrument can be formed on the ends or tips of the instrument (e.g., as identical or different tips of an elongated or rod-shaped instrument that can be moved relative to the instrument holder into at least two fixed or invariable end states). In the at least two fixed end states of the instrument, at least one of the at least two functional elements, such as for example the tips of the instrument, can be protected by the instrument holder (e.g., by the instrument holder surrounding the functional element or the tips by the protected tip or functional element being situated in the interior of the instrument holder). The non-protected functional element or elements can be used for registration procedures. Particularly, only one of the functional elements or only one of the tips can be used in each end state, while the remaining functional elements may be protected by the instrument holder and may not be used.

At least one of the markers can be connected to the instrument or can be arranged directly on the instrument, and at least two markers can be connected to the instrument holder or arranged on the instrument holder. At least one marker arranged on the instrument can be shifted along a longitudinal axis of the pre-calibrated reusable instrument or instrument holder, in particular together with the instrument, and thus change its position relative to the at least two markers arranged on the instrument holder. From the new position of the at least one marker arranged on the instrument relative to at least two markers arranged (preferably fixed) on the instrument holder, it is possible to deduce which functional element or elements can or are being used. In other words, it can be deduced which functional elements are not protected by the instrument holder, or which functional elements cannot be used because they are surrounded or protected by the instrument holder.

In a first end state of the instrument, in which the instrument preferably can not be moved relative to the instrument holder, the at least three markers can form a triangle or polygon, wherein the triangle is not congruent to a triangle formed by the at least three markers in a second end state of the instrument. Due to the difference between the triangles or polygons or the difference in the geometry of the marker arrangement in the end states, a navigation system can ascertain the state of the reusable instrument, and ascertain and/or deduce from this which functional element of the instrument can be or is being used.

In a method for identifying the state of the pre-calibrated reusable instrument, one of at least two possible states or one of at least two possible marker geometries of the reusable instrument can be identified. The identified or current state or the identified or current marker geometry can be ascertained by means of stored information on the geometry of the pre-calibrated reusable instrument. For example, by comparing the current state or the current marker geometry with a plurality of known or stored marker geometries that can be stored in a database or memory, for example, it is possible to deduce which of the functional elements can be or is being used.

The invention further provides a computer program which, when it is loaded onto a computer or is running on a computer, performs a method as described above. The invention also provides a program storage medium or computer program product comprising such a program.

BRIEF DESCRIPTION OF THE DRAWINGS

FIG. 1 illustrates an exemplary pre-calibrated reusable instrument in accordance with the invention, in a first state.

FIG. 2 illustrates the pre-calibrated reusable instrument of FIG. 1, in a second state.

FIG. 3 is a block diagram of a navigation system that can be used with the invention.

FIG. 4 is a block diagram of a computer system that can be used to implement the method of the present invention.

DETAILED DESCRIPTION

FIG. 1 shows an exemplary pre-calibrated reusable instrument 1 that includes a hollow cylindrical instrument holder 2 and a rod-shaped instrument 3 within the holder 2. The instrument 3 includes tips 4, 5 having different shapes, wherein the tips are located at distal ends of the instrument. The tips 4, 5 have a different functionality from one another and can be used before, during, or after surgery for registering different points on the body or bone contours, for example. The instrument 3 can be a pointer instrument wherein the tips 4, 5 can travel or scan and register bodies, such as parts of a patient's body or bones. Due to the different shape of the tips 4, 5 of the pointer instrument, the tips 4, 5 can be used for different tasks, such as registering different contours, bones or parts of the body, such that the instrument 1 having the two-tip pointer has the same functionality as two individual pointers each having one tip.

Two passive or active markers 6, 7 are attached to the instrument holder 2 at positions A and C, while one marker 8 is attached to the instrument 3. In the position or end state B1 of the marker 8, the three markers 6, 7, 8 form a triangle AB1C, if one imagines the markers 6, 7, 8 connected. In the fixed end state B1 of the marker 8, the marker 8 is preferably locked, latched or safety-locked, such that it can only be moved when a latch or safety lock has been released. As can be seen in FIG. 1, one tip 5 of the instrument 3 lies fully in the instrument holder 2 or is surrounded by the instrument holder and, thus, is protected from being touched, damaged or broken. While the tip 5 lies in or is protected by the instrument holder, the other tip 4 can be used for a registration procedure.

The particular tip 4, 5 being used is defined by the geometry of the marker arrangement, in particular by the triangle AB1C formed by the markers 6, 7, 8. The marker arrangement can be detected by a navigation system, for example, and compared with known marker arrangements, such as triangular shapes. This comparison can be performed in a computational unit, for example, such as a computer. Based on the comparison of the current state or the current marker geometry with known states or marker geometries, it is possible to ascertain which tip 4, 5 of the pointer or instrument 3 is being used for registration, so as to take into account specific data of the tip 4, which can be used when registering a body or part of a body such as a bone.

FIG. 2 shows the pre-calibrated reusable instrument from FIG. 1 in a second, preferably fixed or safety-locked end state B2 of the marker 8, wherein the marker arrangement from FIG. 2 can be distinguished from the marker arrangement from FIG. 1 from any spatial direction. The triangle AB2C from FIG. 2, formed by the three markers 6, 7, 8, is not congruent with the triangle AB1C of the marker arrangement from FIG. 1. More specifically, when viewed from any spatial point, the different sides of the two triangles AB1C and AB2C can be determined or and/or different angles of the two triangles AB1C and AB2C can be seen. It is therefore possible, from any spatial point, to clearly distinguish which position, in particular which fixed end state, the marker 8 is situated. From the determined marker position, it is possible to deduce which of the two tips 4, 5 of the pointer or instrument 3 has been extended from the instrument holder 2 or which of the two tips 4, 5 is lying in the instrument holder 2. Further, due to the different shapes of the tips 4, 5, it is possible to deduce which data should be taken into account during a registration procedure, in particular in the calculations of the computational unit.

FIG. 3 illustrates a navigation system 10 that can be used to navigate or track the pre-calibrated reusable instrument 1. The navigation system 10 includes cameras 12, such as infrared cameras, operatively coupled to a computational unit 14. The cameras 12 collect spatial data of the markers 6, 7, 8, and provide this data to the computational unit 14. Using the data, the computational unit 14 ascertains a position in three-dimensional space of the markers and there relative locations with respect to each other. Based on the relative location of the markers, the computational unit ascertains which tip 4, 5 is within the instrument holder 2 and which tip 4, 5 is extended from the instrument holder 2. Further, the navigational system can track the location in three-dimensional space of the tips 4, 5, which then can be used to register a body part, for example.

Moving to FIG. 4, the computational unit 14 for executing a computer program in accordance with the present invention is illustrated in more detail. The computational unit 14 includes a computer 20 for processing data, and a display 22 (e.g., a Cathode Ray Tube, Liquid Crystal Display, or the like) for viewing system information. A keyboard 24 and pointing device 26 may be used for data entry, data display, screen navigation, etc. The keyboard 24 and pointing device 26 may be separate from the computer 20 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 24 and pointing device 26. Touch screens may be beneficial when the available space for a keyboard 24 and/or a pointing device 26 is limited.

Included in the computer 20 is a storage medium 28 for storing information, such as application data, screen information, programs, etc. The storage medium 28 may be a hard drive, an optical drive, or the like. A processor 30, such as an AMD Athlon 64™ processor or an Intel Pentium IV® processor, combined with a memory 32 and the storage medium 28 execute programs to perform various functions, such as data entry, numerical calculations, screen display, system setup, etc. A network interface card (NIC) 34 allows the computer 20 to communicate with external devices.

The actual code for performing the functions described herein can be readily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A pre-calibrated reusable instrument assembly, comprising:
    an instrument holder;
    an instrument held by and movable with respect to the instrument holder between first and second positions, said instrument comprising at least two functional elements, one of the functional elements being positioned for use when the instrument is in the first position, and the other being positioned for use when the instrument is in the second position; and
    at least three markers trackable by a medical navigation system, including a first marker moveable with the instrument holder and a second marker movable with the instrument relative to the first marker on the instrument holder such that a movement of the instrument produces a corresponding movement of the second marker between positions respectively corresponding to the first and second positions of the instrument, whereby the navigation system can determine which functional element is positioned for use.

2. The pre-calibrated reusable instrument assembly as set forth in claim 1, wherein a positional relationship between the at least three markers is indicative of which of the at least two functional elements is positioned for use.

3. The pre-calibrated reusable instrument assembly as set forth in claim 1, wherein the instrument holder is a grip for the pre-calibrated reusable instrument assembly.

4. The pre-calibrated reusable instrument assembly as set forth in claim 1, wherein the instrument is mounted within the instrument holder such that the instrument can be shifted with respect to the instrument holder.

5. The pre-calibrated reusable instrument assembly as set forth in claim 1, wherein the instrument can be shifted along a longitudinal axis of the instrument or the instrument holder.

6. The pre-calibrated reusable instrument assembly as set forth in claim 1, wherein the instrument is non-rotatably mounted in the instrument holder.

7. The pre-calibrated reusable instrument assembly as set forth in claim 1, wherein the instrument can be moved into at least two fixed end states.

8. The pre-calibrated reusable instrument assembly as set forth in claim 7, wherein in the at least two fixed end states of the instrument, at least one of the at least two functional elements is protected by the instrument holder.

9. The pre-calibrated reusable instrument assembly as set forth in claim 1, wherein the at least two functional elements of the instrument are different from each other.

10. The pre-calibrated reusable instrument assembly as set forth in claim 1, wherein the at least two functional elements are formed on ends or tips of the instrument.

11. The pre-calibrated reusable instrument assembly as set forth in claim 1, wherein the second marker is arranged on the instrument.

12. The pre-calibrated reusable instrument assembly as set forth in claim 1, wherein the first and another of said at least three markers are arranged on the instrument holder.

13. The pre-calibrated reusable instrument assembly as set forth in claim 1, wherein in a first end state of the instrument the at least three markers form a first triangle, and in a second end state of the instrument the at least three markers form a second triangle, wherein the first triangle and the second triangle are not congruent.

14. A method for identifying a state of a pre-calibrated reusable instrument assembly, wherein the instrument assembly includes an instrument holder, an instrument held by and movable with respect to the instrument holder between first and second positions, said instrument comprising at least two functional elements, one of the functional elements being positioned for use when the instrument is in the first position, and the other being positioned for use when the instrument is in the second position, and at least three markers trackable by a medical navigation system, including a first marker moveable with the instrument holder and a second marker movable with the instrument relative to the first marker on the instrument holder such that a movement of the instrument produces a corresponding movement of the second marker between positions respectively corresponding to the first and second positions of the instrument, comprising:

identifying one of at least two possible marker geometries of the pre-calibrated reusable instrument;

comparing the one identified geometry to pre-stored geometrical information of the pre-calibrated reusable instrument; and ascertaining the state of the pre-calibrated reusable instrument assembly based on the comparison.

15. A computer program embodied on a non-transitory computer-readable medium for identifying a state of a pre-calibrated reusable instrument assembly, wherein the instrument assembly includes an instrument holder, an instrument held by and movable with respect to the instrument holder, said instrument including at least two functional elements, and at least three markers, wherein at least one of the markers is movable with the instrument relative to the instrument holder such that a movement of the instrument produces a corresponding movement of the at least one marker, comprising code that causes a processor to implement a method as set forth in claim 14.

16. A system for identifying a state of a pre-calibrated reusable instrument assembly, wherein the instrument assembly includes an instrument holder, an instrument held by and movable with respect to the instrument holder between first and second positions, said instrument including at least two functional elements, one of the functional elements being positioned for use when the instrument is in the first position, and the other being positioned for use when the instrument is in the second position, and at least three markers trackable by a medical navigation system, including a first marker moveable with the instrument holder and a second marker movable with the instrument relative to the first marker on the instrument holder such that a movement of the instrument produces a corresponding movement of the second marker between positions respectively corresponding to the first and second positions of the instrument, comprising:

a processor circuit having a processor and a memory;

an identification sub-system stored in the memory and executable by the processor, the identification sub-system comprising:

logic that identifies one of at least two possible marker geometries of the pre-calibrated reusable instrument assembly;

logic that compares the one identified geometry to pre-stored geometrical information of the pre-calibrated reusable instrument assembly; and logic that ascertains the state of the pre-calibrated reusable instrument assembly based on the comparison.

* * * * *